United States Patent
Hahn et al.

(10) Patent No.: US 7,331,703 B1
(45) Date of Patent: Feb. 19, 2008

(54) VISCOSITY CONTROLLER FOR INK PAD PRINTERS

(75) Inventors: Ronald Hahn, Erie, PA (US); Steve Bullock, Erie, PA (US); Robert W. Heiges, Waterford, PA (US)

(73) Assignee: Automated Industrial Systems

( * ) Notice: Subject to any disclaimer, the term of this patent is extended or adjusted under 35 U.S.C. 154(b) by 693 days.

(21) Appl. No.: 10/876,797

(22) Filed: Jun. 28, 2004

(51) Int. Cl.
*B01F 15/02* (2006.01)
*G01N 11/14* (2006.01)
*G05D 24/00* (2006.01)

(52) U.S. Cl. .................... 366/152.5; 73/54.31; 137/92

(58) Field of Classification Search ............ 366/152.1, 366/152.3, 152.5, 155.1, 160.1, 168.1, 601; 73/54.31, 54.32, 54.33, 54.28; 137/92; 101/364, 101/365, DIG. 34
See application file for complete search history.

(56) References Cited

U.S. PATENT DOCUMENTS

| | | | |
|---|---|---|---|
| 3,596,672 A | | 8/1971 | McBee |
| 4,363,742 A | * | 12/1982 | Stone |
| 4,436,431 A | * | 3/1984 | Strong et al. |
| 4,484,468 A | | 11/1984 | Gau et al. |
| 4,735,227 A | * | 4/1988 | Royse et al. |
| 5,236,263 A | * | 8/1993 | Friedland |
| 5,677,481 A | * | 10/1997 | Brown et al. |
| 6,102,507 A | | 8/2000 | Yoshida |
| 6,536,341 B2 | | 3/2003 | Shiki et al. |
| 6,546,866 B1 | * | 4/2003 | Adachi et al. |
| 2002/0167555 A1 | | 11/2002 | Miura et al. |

FOREIGN PATENT DOCUMENTS

| | | | |
|---|---|---|---|
| DE | 36 02 309 | | 7/1987 |
| JP | 56-19765 | | 2/1981 |
| JP | 57-14080 | | 1/1982 |
| JP | 58-20454 | * | 2/1983 |
| JP | 59-87161 | | 5/1984 |
| JP | 60-34869 | | 2/1985 |
| JP | 2006-35587 | * | 2/2006 |

* cited by examiner

*Primary Examiner*—Charles E. Cooley (57) ABSTRACT

A viscosity controller automatically monitoring and controlling the viscosity of ink in a pad printing device on a continuous basis throughout the printing process includes a sealed ink cup having mounted thereon a motor with a paddle extending into the ink cup, a solvent tank in flow communication with the ink cup, and a valve for allowing selective amounts of the solvent to be added to the ink cup from the solvent tank. The viscosity of the ink in the cup creates torque on the paddle that affects the number of encoder pulses that are counted per time period by a motor encoder mounted to the motor, and the encoder pulses are counted and compared to a look up table stored in the microprocessor of the controller to determine if the valve should be opened to add diluting agent to the ink cup so that the ink viscosity can be maintained at a preset or predetermined value.

18 Claims, 7 Drawing Sheets

Fig. 9 ced VISCOSITY CONTROLLER FOR INK PAD
PRINTERS

FIELD OF THE INVENTION

The present invention pertains to the regulation of the viscosity of ink in an ink pad printing application, and more particularly pertains to a viscosity controller for continuously monitoring, controlling and incrementally adjusting the viscosity of ink for a pad printing apparatus throughout the printing process.

BACKGROUND OF THE INVENTION

In various kinds of pad printing and press printing operations determining the dilutability or viscosity of the relevant preparation is a crucial factor in achieving high print quality. Generally before the printing operation commences a value that may be referred to as a viscosity reference value is set or determined as the value at which the ink viscosity should be maintained. It is common for the viscosity of the preparation to change considerably during the printing application, and thus a diluting agent must be added to the preparation for maintaining the desired viscosity. This occurs in pad ink printing where it is known that the surface viscosity of the preparation is susceptible to abrupt changes.

Manual methods of maintaining the desired viscosity include mixing the diluting agent into the preparation and then taking measurements at given time periods to determine the viscosity. If the viscosity exceeded the desired reference value measured amounts of the diluting agent would be manually added in order to achieve the reference value in a trial and error method. In addition, graphical and mathematical tables and registers can be prepared that are specific for each preparation and diluting agent system. However, these methods are laborious and prone to methodological errors.

The Kellner Patent (German Patent 3,602,309) discloses an apparatus for determining the dilutability of viscous preparations that are particularly used in intaglio and flexographic printing inks. The Kellner Patent includes a flowmeter with a diluting agent counter mounted on the diluting agent tube. A reference value sensor, a start button, a timer and a sensor having a rotator immersed in a sample vessel are linked so that after the timer is activated and a preset interval elapses, a valve opens and the diluting agent's flow rate is displayed. As soon as the actual value of the viscosity attains the reference value, the valve closes and the counter for the diluting agent can be returned to the zero position. It should be noted that in the Kellner Patent the addition of the diluting agent doesn't occur until the appropriate thixotropic reduction of the preparation is achieved.

SUMMARY OF THE INVENTION

The present invention comprehends a viscosity controller for ink pad printers for incrementally adjusting the viscosity of the ink present in the ink cup of the ink pad printer. The viscosity controller includes a sealed ink cup to which a viscosity motor assembly is mounted. The viscosity motor assembly includes a DC motor having a shaft extending into the ink cup, and mounted to the shaft end is a paddle for continuously agitating the ink. An encoder is mounted to the motor and is interconnected to the shaft whereupon each rotation of the shaft generates a given number of encoder pulses that are counted by a counter; the counter counts the number of encoder pulses for a discrete time period, and then compares that number to a look up table in the software of the controller to determine if the ink is too thick and a valve in the solvent line will be opened to allow solvent to flow from a solvent tank and through the solvent line to the ink cup. Sampling can occur once a minute by the controller for comparing the average number of encoder pulses with the software look up table, and if it is automatically determined by the controller that the viscosity of the ink has increased, or is greater than desired, the valve is opened for a given time period to add solvent to the ink cup. Intermixing of the solvent and ink within the sealed cup occurs for a given time period, for example, one minute, before the viscosity reference number is compared to the encoder pulses to gauge whether more solvent should be added to bring the viscosity of the ink in line with the viscosity reference number.

It is an object of the present invention to provide a viscosity controller for ink pad printers that increases the productivity of the printers.

It is another object of the present invention to provide a viscosity controller for ink pad printers that gives a consistent print quality throughout the particular printing process or run.

It is still another object of the present invention to provide a viscosity controller for ink pad printers that overcomes physical conditions and factors such as humidity and pressure that can impair the printing process.

It is still yet another object of the present invention to provide a viscosity controller for ink pad printers that permits fast color changeover and cleanup.

It is still yet a further object of the present invention to provide a viscosity controller that it capable of retrofitting to most types of sealed cup pad printers.

A yet still further object of the present invention is to provide a viscosity controller for ink pad printers that automatically controls the ink viscosity without operator intervention.

Yet another object of the present invention is to provide a viscosity controller for ink pad printers that maintain ink viscosity by setting the desired parameters for ink viscosity in the viscosity controller's control program.

Yet still another object of the present invention is to provide a viscosity controller for ink pad printers wherein the ink viscosity is continuously monitored and compared to the pre-selected value as input through the control program.

Yet still a further object of the viscosity controller for ink pad printers is the ability of the viscosity controller to determine when ink viscosity exceeds desired levels so that thinning solvent can be intermixed with the ink thereby returning the ink viscosity to the original pre-selected value.

These and other objects, features, and advantages will become apparent to one skilled in the art upon a perusal of the following detailed description read in conjunction with the following drawing figures.

DETAILED DESCRIPTION OF THE PREFERRED EMBODIMENT

Figure 6:
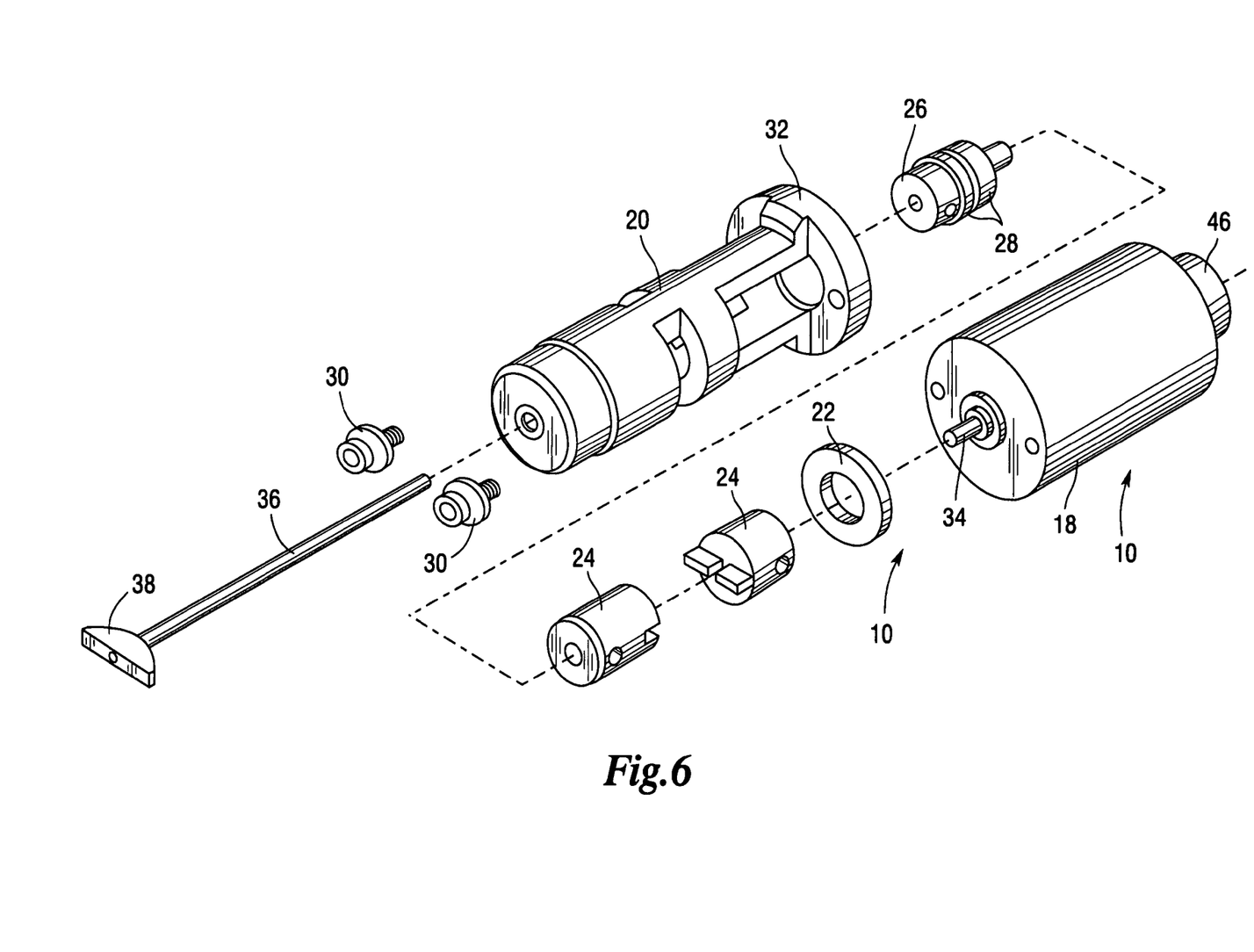
FIG. 6 is an exploded view of the viscosity controller illustrating the arrangement and interconnections of the paddle, the motor assembly and the encoder.

Illustrated in FIGS. 1 through 9 is a viscosity controller 10 for monitoring, controlling and incrementally adjusting the viscosity of ink used by a pad printing apparatus throughout a printing application. Viscosity controller 10 of the present invention does not physically measure the amount of ink in the pad cup, but, instead, incrementally adjusts the viscosity of the ink, on a continual basis throughout the work shift, to maintain ink viscosity at a preset or predetermined level or value particular for that application. Illustrated in FIGS. 1 through 6 are the primary structural elements of the preferred embodiment of viscosity controller 10 of the present invention. Thus, a sealed ink cup 12 includes a reservoir 14 for holding the ink that is used in the printing process or application. Ink cup 12 includes structural elements located at the cup center for attaching ink cup 12 to the pad printing machines and as these are conventional in the field they are not shown. Mounted in sealed registration to ink cup 12 is a viscosity motor assembly 16 that includes in the preferred embodiment a DC permanent magnet motor 18. As shown in FIG. 6, in order to properly mount motor 18 to ink cup 12, a motor mount adapter 20 is used as an intermediate mounting structure. Motor 18 is mounted to motor mount adapter 20 by employing a motor spacer 22, a pair of couplings 24, and a bearing mount adapter 26 having bearings 28 mounted thereon. A pair of fasteners 30 is inserted through the flange 32 of motor mount adapter 20 for securing motor mount adapter 20 to motor 18. A motor shaft 34 extends from the end of motor 18 for engagement to bearing mount adapter 26.

As shown in FIGS. 1 and 4 through 6, a primary shaft 36 axially extends through motor mount adapter 20 so that shaft 36 can be coupled to and driven by motor 18. Mounted to the distal end of shaft 36 is a paddle or impeller 38 that is submerged in the ink for continuously stirring and agitating the ink in cup 12. Paddle 38 has a pyramidal shape for reducing the total surface area of paddle 38 that interacts with the ink thereby reducing the torque required, and the pyramidal shape eliminates the problem of cavitation that occurs about paddle 38 as paddle 38 rotates.

Figure 1:
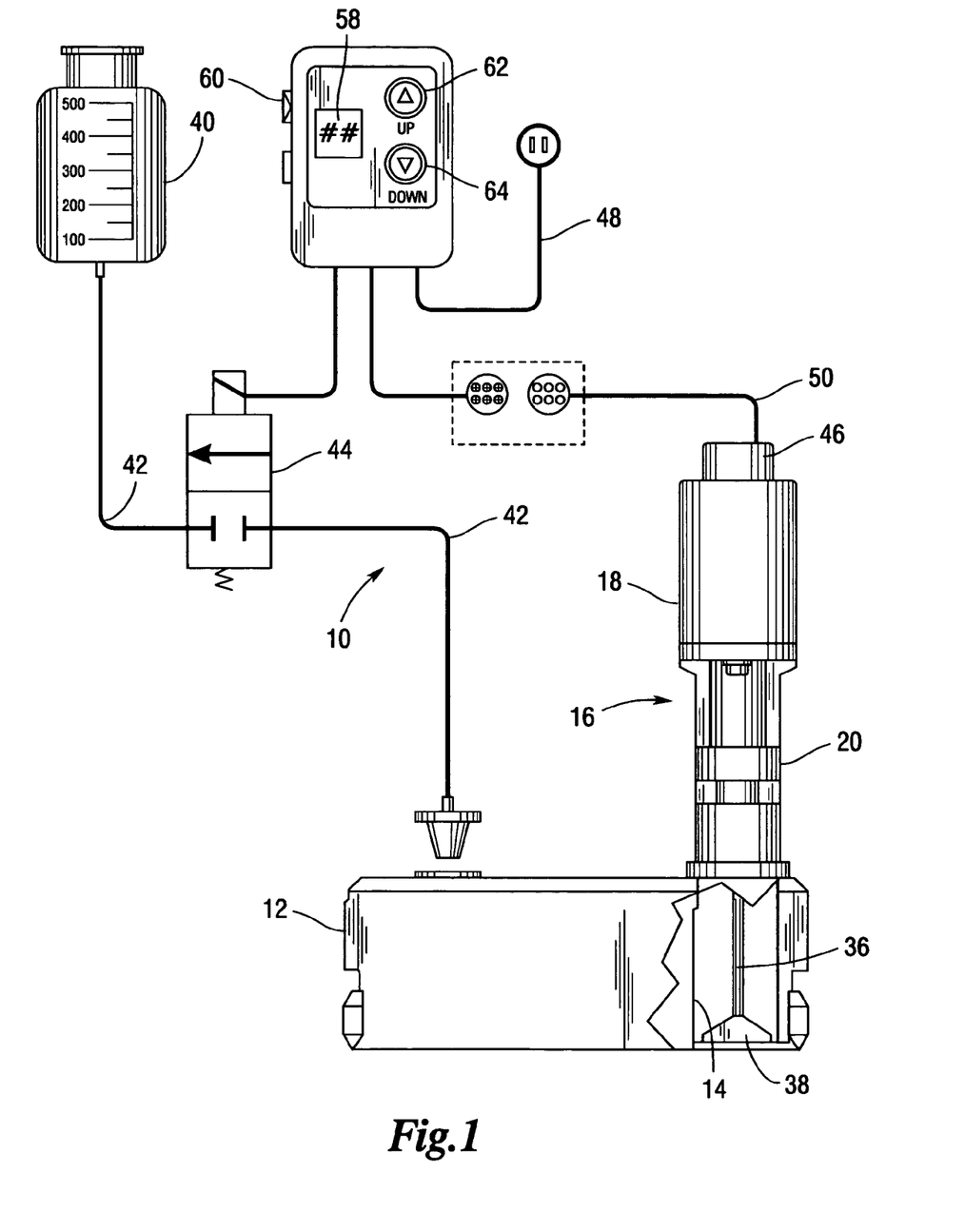
FIG. 1 is a schematic elevational view of the viscosity controller for ink pad printers of the present invention.
Figure 2:
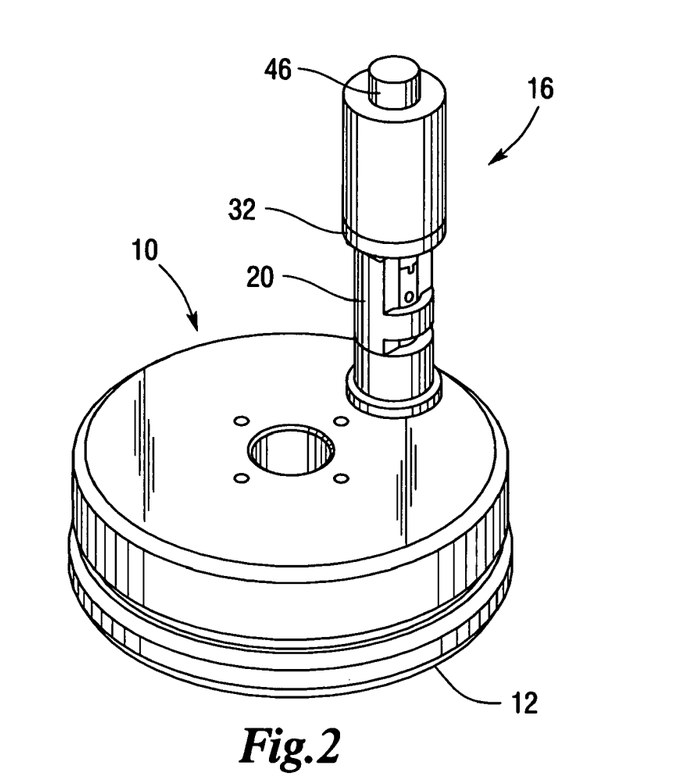
FIG. 2 is a perspective view of the viscosity controller illustrating the mounting of the viscosity motor assembly to the ink cup.
Figure 3:
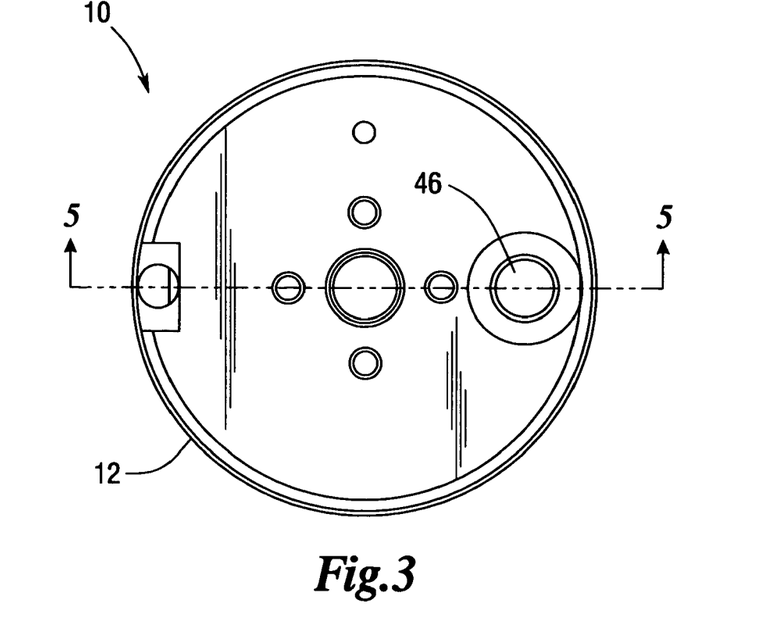
FIG. 3 is a top plan view of the ink cup for the viscosity controller.
Figure 4:
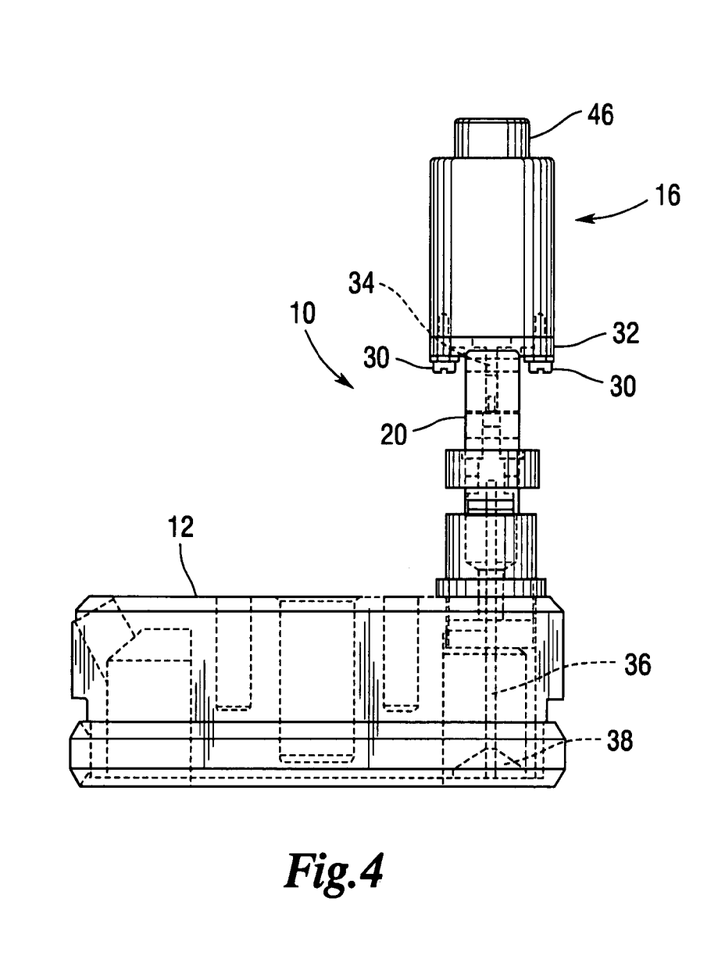
FIG. 4 is a side elevational view of the viscosity controller illustrating the securement of the motor assembly to the ink cup, and other elements of the ink cup in hidden line.
Figure 5:
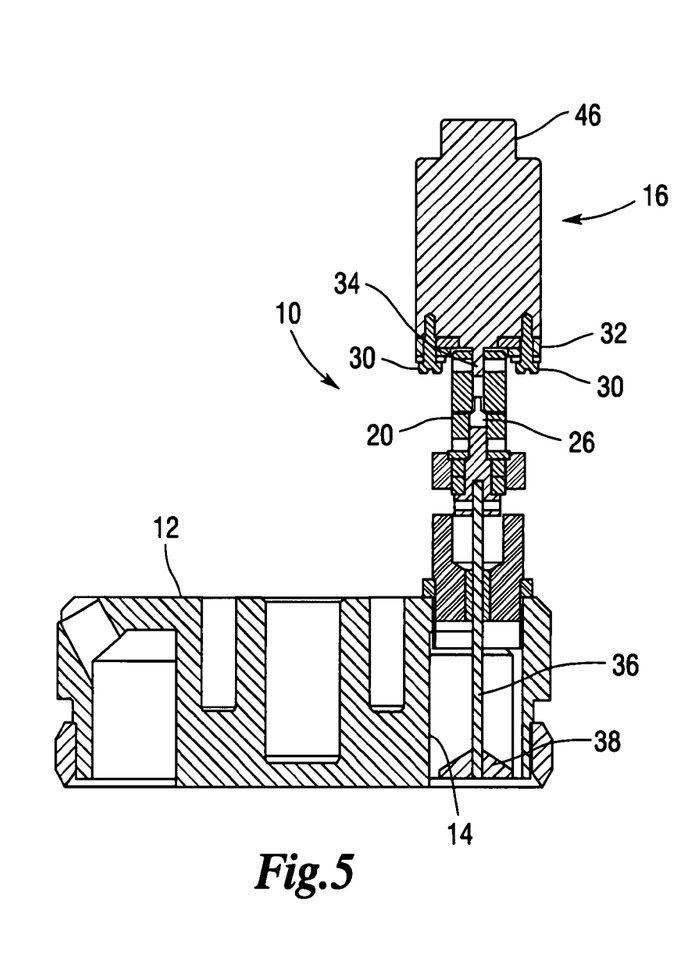
FIG. 5 is a sectioned elevational view of the ink cup and motor assembly taken along lines 5—5 of FIG. 3.

As shown in FIG. 1, a solvent tank or reservoir 40 is mounted adjacent to ink cup 12 and is in flow communication with ink cup 12 by a solvent line 42. Among the most common solvents used with pad printing inks are thinners, reducers, and ink cleaners such as PMA glycol ether, xylene, ethyl benzene, glycol ether acetate, and acetone. A valve 44 is placed in solvent line 42 and valve 44 can be selectively and automatically opened for regulating and controlling the flow of solvent to ink cup 12 by addition of predetermined amounts of solvent to the ink for maintaining the desired viscosity of the ink. In the present embodiment valve 44 is a two-way 24 v DC valve.

Illustrated in FIGS. 1 through 6 is an encoder 46 that is located on top of motor 18. Encoder 46 is a 5-volt encoder that is coupled to motor shaft 34, and motor shaft 34 is coupled to shaft 36 of paddle 38 to rotate paddle 38. Encoder 46 generates a fixed number of pulses per revolution of paddle 38, and which in the present embodiment is 16 pulses per revolution of paddle 38. In operation the motor speed (as determined by the power supply voltage) falls as the load increases (increase in ink viscosity); and as the motor load increases, the current required by motor 18 goes up causing the power supply voltage to fall causing motor 18 to slow down thus reducing the number of encoder pulses per unit of time. This reduction in encoder pulses initiates actions hereinafter described that cause solvent to be added to the ink.

In the preferred embodiment of the invention viscosity controller 10 includes a microprocessor for continuously monitoring, observing, comparing and regulating data received from encoder 46 in order to determine when amounts of solvent should be added to the ink by initiating the opening of valve 44 or by keeping valve 44 closed so that no solvent flows into ink cup 12. The microprocessor is a PIC16F84 microcontroller, and viscosity controller 10 includes a power cord 48 for plugging into a 120VAC outlet and motor assembly cable 50 for interconnecting the microprocessor to encoder 46 and motor 18 of motor assembly 16. The micro controller includes various software routines such as a measurement algorithm for counting the encoder pulses in order to arrive at an average number of pulses that is converted to decimal form and then stored and displayed as the "actual viscosity number"—referred to as the "AVIS-CNO" as illustrated in the flowcharts 52, 54 and 56 of FIGS. 7, 8 and 9. FIG. 1 shows viscosity controller display 58 for displaying to the operator system parameters such as the actual viscosity number. Viscosity controller 10 also includes an on/off switch 60 and an up button 62 and a down button 64. Up and down buttons 62 and 64 are used by the operator to preset the ink viscosity at a certain value, referred to as the viscosity reference number. This is the number, value, or level the ink viscosity is to be maintained at during the printing application, and to which after given time periods the actual viscosity number is compared to determine whether or not amounts of solvent should be added to the ink. In addition, viscosity controller 10 includes four different alarm modes for signaling to the operator various conditions occurring relative to the ink viscosity and the system.

Figure 7:
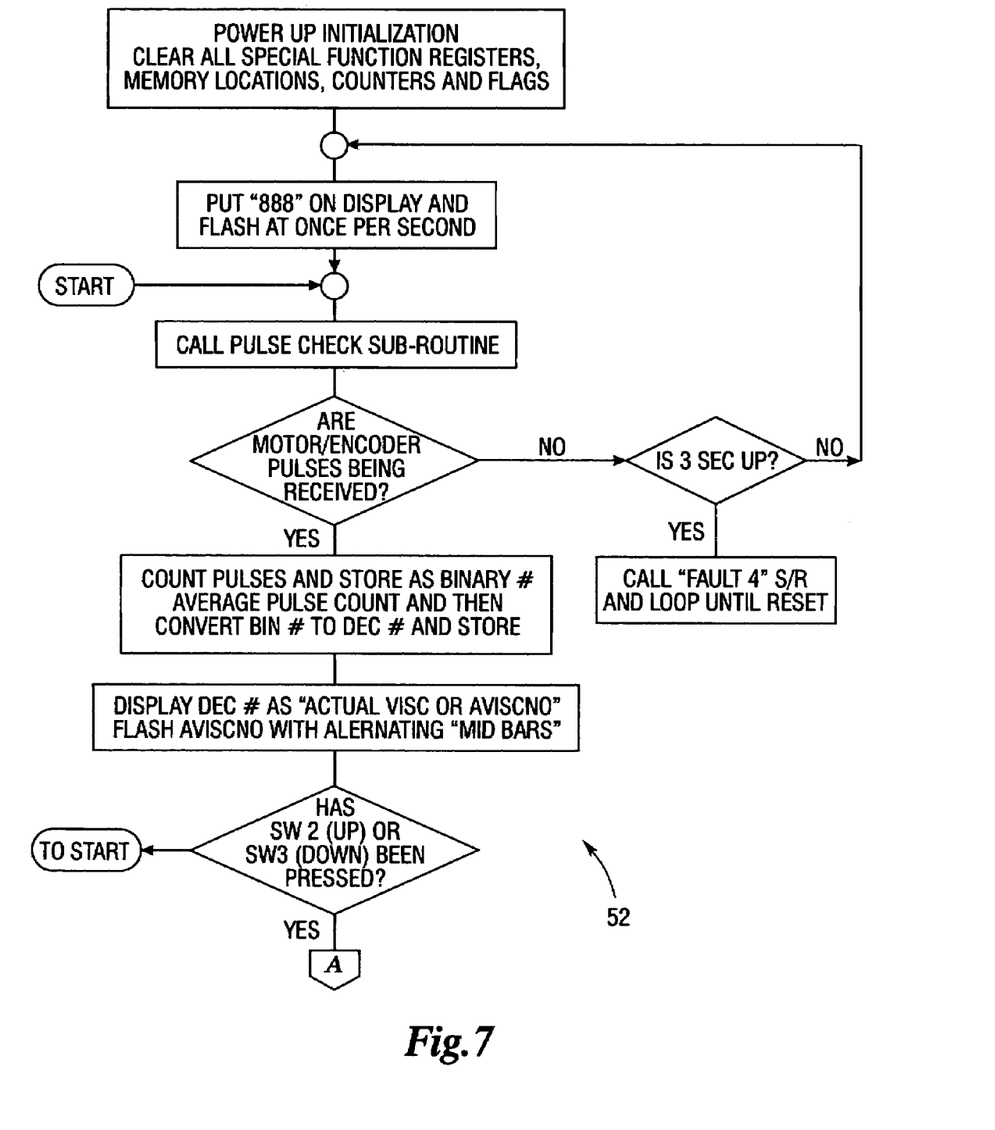
FIG. 7 is a flowchart for the viscosity controller illustrating the controller steps for initializing the system, and for counting, storing and averaging the pulse counts so that they can be displayed as an actual or average viscosity number.
Figure 8:
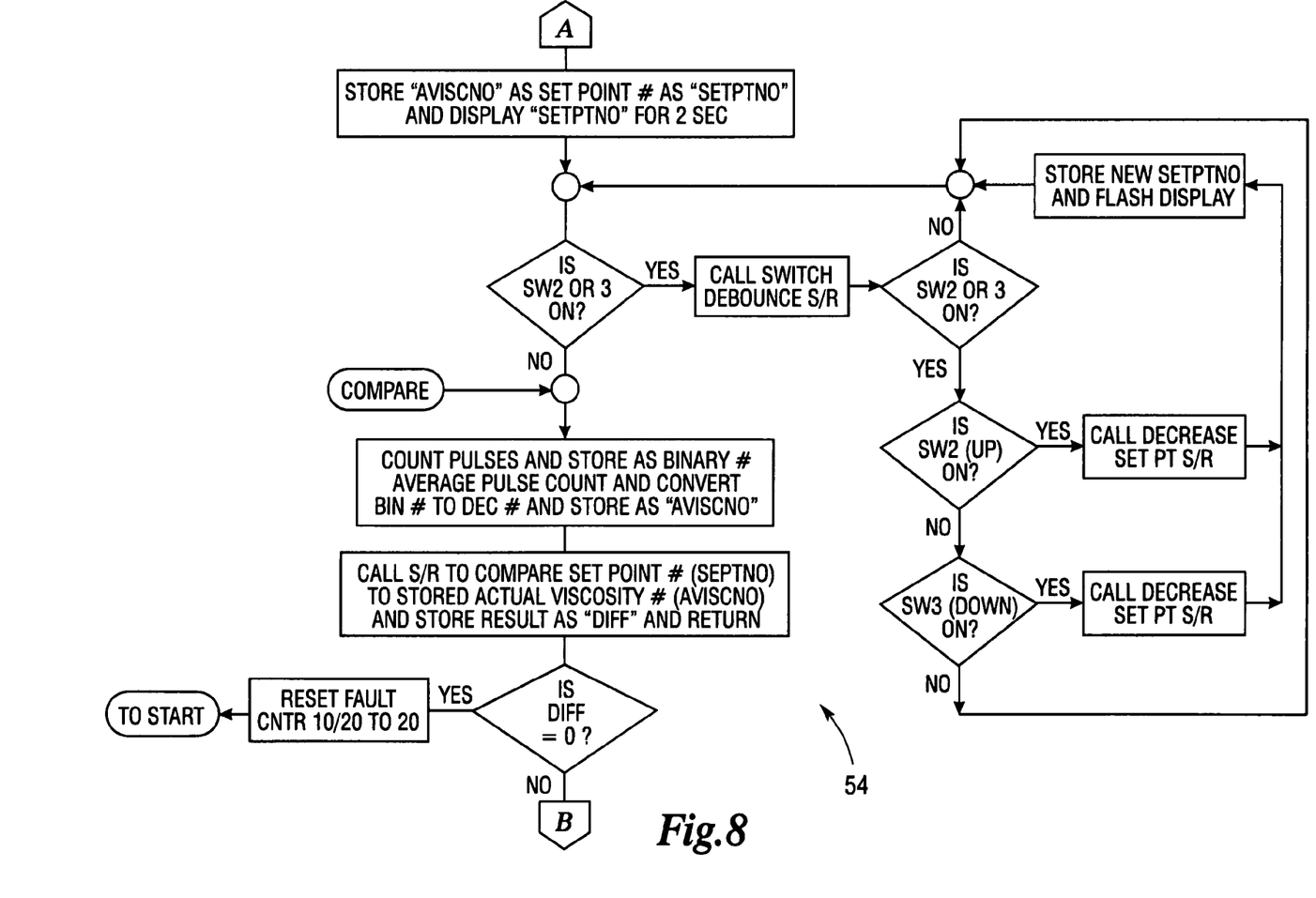
FIG. 8 is a flowchart for the viscosity controller illustrating the controller steps for counting and storing the pulses as an average pulse count and then comparing the stored set point value with the actual viscosity number to determine if they are the same or differ; and, FIG. 9 is a flowchart for the viscosity controller illustrating the controller steps for turning the valve on to allow more solvent into the ink cup dependent upon an evaluation of the relationship between the stored set point number and the actual viscosity number.
Figure 9:
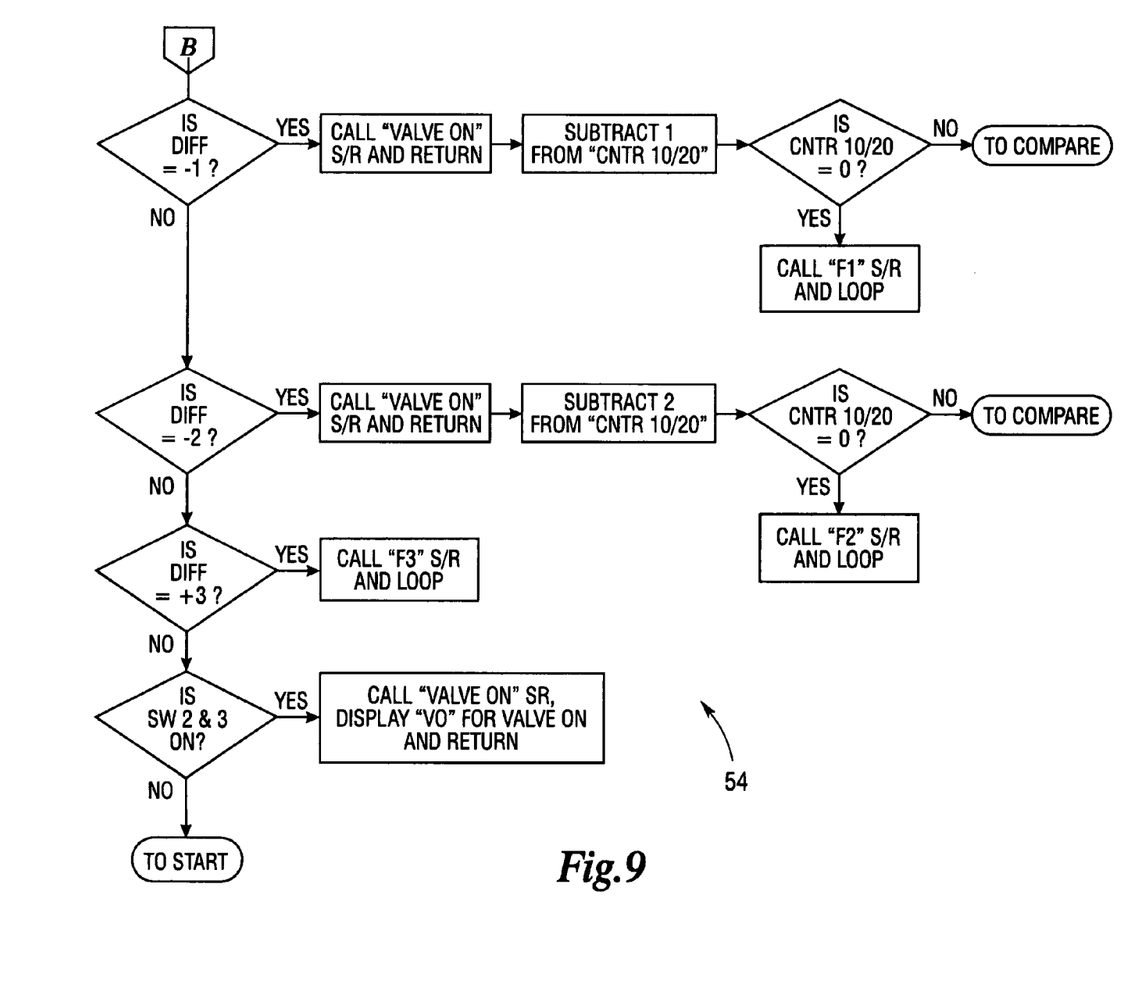

The microprocessor software, as embodied in flowcharts 52, 54, and 56, includes a reference scale or look-up table for measuring and comparing the viscosity in the ink during one minute time periods a number of times throughout a production shift. The preferred viscosity reference number scale has a range of between 7 and 42 where the lower end is commensurate with the viscosity of oxygen and the upper end is commensurate with the viscosity of coal tar. The purpose of the scale range, and the range of discrete numbers encompassed by the scale, is twofold: 1) provide a real time indication of the viscosity of the ink in ink cup 12 so that the operator can monitor the printing process and observe that the ink viscosity is being automatically maintained at the desired level—at preset viscosity reference number—so that the operator can manually adjust the ink viscosity by using the front panel buttons and read changes in the reference scale numbers appearing on display 58; and 2) if the ink that is being used for the particular job has been run in the past, and the operator has recorded the optimal viscosity settings or values, the operator can preset the desired viscosity by referring to those numbers and set the viscosity he wants to maintain using the up and down buttons 62 and 64 on the controller panel. FIG. 7 illustrates flow chart 52 for system initialization, motor 18 and encoder 46 checks, and the counting and storing of the encoder pulses and displaying the counted pulses per time period as the "AVISCNO". Flowchart 54 of FIG. 8 illustrates the steps for comparing the "AVISCNO" with the stored set point number that can be the preset by the operator to determine if there is a difference from the actual viscosity number. If there is a difference then the routine shown in flowchart 56 in FIG. 9 is called for automatically opening valve 44 to add fixed amounts of solvent to the ink so that the actual viscosity number returns to the desired viscosity level—the set point number (SETPTNO).

In general for most eight-hour work shifts ink cup 12 does not need to be refilled, so the viscosity of the ink, which must be exactly maintained for pad printing jobs, has time to fluctuate from the desired value or set point number. However, heavy printing jobs may require refill every two hours. Thus, in operation a desired viscosity reference number can be preset or pre-selected by using the up and down buttons 62 and 64 on controller 10. Paddle 38 is immersed in ink cup 12 and the printing operation commences with encoder 46 transmitting encoder pulses to the microprocessor. Once a minute per time period the number of encoder pulses are counted, stored and compared to a value stored in the look-up table of the microprocessor software. Using the steps and routines of flowcharts 52, 54, and 56 the microprocessor compares the average number of encoder pulses, stored and displayed as the AVISCNO (actual viscosity number), with the SETPNO, the viscosity set point number. The automatic control and maintenance of the ink viscosity occurs in this comparison and subsequent decision steps. Thus, if it is determined that the ink viscosity has increased, the microprocessor software routine shown in flowchart 56 of FIG. 9 actuates valve 44 to open for ½ second so that solvent can be added to ink cup 12. The microprocessor permits the adjustment of this time interval for opening valve 44. The solvent is intermixed with the ink for one minute before the preset viscosity number or set point number is compared to the actual viscosity number generated by the encoder pulses to determine if more solvent needs to be added. The adjustments to maintain the desired ink viscosity are made with the addition of one or two drops of solvent at a time. Over the course of a printing operation, and because of the continuous and automatic monitoring and adjusting of the viscosity to maintain the desired level, perhaps only 6 to 12 drops of solvent may need to be added during an eight hour shift.

While the invention has been described with respect to a preferred embodiment, it will be clear to those skilled in the art that numerous modifications, alterations, and variations may be made to the invention without departing from the spirit and scope of the invention; and that the invention is not to be limited by the specific illustrative embodiment, but only by the spirit and scope of the appended claims.

We claim:

1. A viscosity controller for continuously monitoring and adjusting the ink viscosity for a pad printing apparatus to maintain optimal ink viscosity throughout the printing application, comprising:
    a paddle for stirring the ink contained with the reservoir of the ink cup of the pad printing apparatus;
    a primary shaft attached to the paddle and extending into the reservoir of the ink cup;
    a motor coupled to the primary shaft for rotating the paddle;
    an encoder interconnected to the motor for generating a fixed number of encoder pulses for each rotation of the shaft;
    a solvent tank in flow communication with the ink cup for incrementally dispensing fixed amounts of solvent to the ink cup for diluting the viscosity of the ink;
    a valve disposed between the solvent tank and the ink cup that can be selectively opened and closed to allow solvent to flow into the ink cup and to prevent the flow of solvent into the ink cup;
    a microprocessor in electrical interconnection with the encoder, the motor and the valve so that the microprocessor can continuously monitor the ink viscosity and count the number of encoder pulses transmitted from the encoder per time period storing that number as the actual viscosity number and comparing the actual viscosity number to a pre-selected set point number that represents the desired ink viscosity level for determining if there is a difference thus resulting in the automatic opening of the valve to allow solvent into the ink cup to adjust the ink viscosity so that the ink viscosity returns to the level represented by the set point number; and,
    a display panel for displaying the actual viscosity number to the operator so that the operator can be continuously apprised of the ink viscosity.

2. The viscosity controller of claim 1 wherein the paddle is triangular-shaped for reducing the surface area interacting with the ink and for eliminating the effects of cavitation that occur about the paddle as the paddle rotates in the ink.

3. The viscosity controller of claim 2 wherein the motor is a DC permanent magnet motor.

4. The viscosity controller of claim 3 wherein the number of encoder pulses counted by the microprocessor for each rotation of the paddle in the ink is 16 pulses per paddle rotation.

5. The viscosity controller of claim 4 further comprising a pair of buttons for allowing the operator to determine the ink viscosity to be maintained during a printing application by selectively using the buttons to pre-set the viscosity set point number for the microprocessor.

6. The viscosity controller of claim 5 wherein the microprocessor will compare the actual viscosity number to the viscosity set point number once each minute for the time period of the printing application to determine if solvent should be added to the ink.

7. The viscosity controller of claim 6 wherein the microprocessor includes a viscosity reference scale that has a range of between 7 and 42 with 7 denoting the viscosity of air and 42 denoting the viscosity of coal tar.

8. The viscosity controller of claim 7 wherein the valve is opened for ½ second to allow solvent to be added to the ink after the microprocessor has determined that the ink viscosity has increased with respect to the viscosity set point number.

9. A viscosity controller for continuously monitoring and adjusting the viscosity of the ink used in a pad printing apparatus for maintaining the desired ink viscosity throughout the print job, comprising:

a paddle for stirring the ink contained within the reservoir of the ink cup of the pad printing apparatus;

a primary shaft attached to the paddle and extending into the reservoir of the ink cup;

a motor coupled to the primary shaft for rotating the paddle;

an encoder interconnected to the motor for generating a fixed number of encoder pulses for each rotation of the shaft;

a solvent tank in flow communication with the ink cup for incrementally dispensing fixed amounts of solvent to the ink cup for diluting the viscosity of the ink;

a valve disposed between the solvent tank and the ink cup and that can be selectively opened to allow solvent to flow from the solvent tank to the ink cup and selectively closed to prevent solvent from entering the ink cup; and a microprocessor in electrical interconnection with the encoder, the motor and the valve so that the microprocessor can continuously monitor the ink viscosity and count the number of encoder pulses transmitted from the encoder each time period throughout the printing job and store that number as the actual viscosity number so that the actual viscosity number can be compared to a pre-selected viscosity set point number that represents the desired ink viscosity level for determining if there is a difference thus resulting in the automatic opening of the valve to allow solvent into the ink cup for adjusting the ink viscosity so that the ink viscosity returns to the level represented by the viscosity set point number.

10. The viscosity controller of claim 9 further comprising a display panel for displaying the actual viscosity number to the operator so that the operator can be continuously apprised of the ink viscosity.

11. The viscosity controller of claim 10 wherein the paddle is triangular-shaped for reducing the surface area of the paddle that interacts with the ink and for eliminating the effects of cavitation that occur in the vicinity of the paddle as the paddle rotates in the ink.

12. The viscosity controller of claim 11 wherein the motor is a DC permanent magnet motor.

13. The viscosity controller of claim 12 wherein the number of encoder pulses counted by the microprocessor for each rotation of the paddle on the shaft is 16 pulses per paddle rotation.

14. The viscosity controller of claim 13 further comprising a pair of buttons for allowing the operator to set the ink viscosity to maintained during the printing job by selectively using the buttons to pre-set the viscosity set point number to which the actual viscosity number is compared for each time period a number of times throughout the print job process.

15. The viscosity controller of claim 14 wherein the microprocessor compare the actual viscosity number to the viscosity set point number once each minute a number of times throughout the printing process to determine if solvent should be added to the ink to bring the viscosity back to the viscosity set point number.

16. The viscosity controller of claim 15 wherein the microprocessor includes a viscosity reference scale that has a range of between 7 and 42 with 7 denoting the viscosity of air and 42 denoting the viscosity of coal tar.

17. The viscosity controller of claim 16 wherein the valve automatically opens for ½ second to allow solvent to be added to the ink upon the microprocessor determining that the ink viscosity has exceeded the viscosity set point number.

18. A method of maintaining the desired ink viscosity for a pad printing apparatus throughout the printing application by using a viscosity controller comprises the steps of:

stirring the ink contained within an ink cup with a paddle immersed therein;

rotating the paddle with a motor coupled to the paddle;

generating a fixed number of pulses for each revolution of the paddle by an encoder;

counting the number of pulses each time period a number of times by a microprocessor in electrical interconnection with the motor and the encoder;

storing the number of pulses counted each time period a number of times throughout the printing application in the microprocessor as the actual viscosity number;

comparing the actual viscosity number to a viscosity set point number in a look-up table in the microprocessor to determine if a difference exists between the two numbers;

adjusting the ink viscosity if a difference exists between the two numbers so that the ink viscosity can be returned to the viscosity set point number by opening a valve to allow solvent to flow from a solvent tank to the ink cup for intermixing with the ink;

checking the ink viscosity level after a fixed time period has elapsed to ascertain if more solvent is required in order to return the ink viscosity to the viscosity set point number.

\* \* \* \* \*